US012674793B2

(12) United States Patent
Birkle et al.

(10) Patent No.: US 12,674,793 B2
(45) Date of Patent: Jul. 7, 2026

(54) SOURCE DETERMINATION OF PRODUCED WATER FROM OILFIELDS WITH ARTIFICIAL INTELLIGENCE TECHNIQUES

(71) Applicant: SAUDI ARABIAN OIL COMPANY, Dhahran (SA)

(72) Inventors: Peter Birkle, Dhahran (SA); Leyla Ismailova, Moscow (RU); Egor Tirikov, Moscow (RU); Maram Saif, Dhahran (SA); Mustafa Ali H Al Ibrahim, Safwa (SA)

(73) Assignee: SAUDI ARABIAN OIL COMPANY, Dhahran (SA)

(*) Notice: Subject to any disclaimer, the term of this patent is extended or adjusted under 35 U.S.C. 154(b) by 323 days.

(21) Appl. No.: 18/260,019

(22) PCT Filed: Jul. 21, 2022

(86) PCT No.: PCT/RU2022/000231
§ 371 (c)(1),
(2) Date: Jun. 29, 2023

(87) PCT Pub. No.: WO2024/019629
PCT Pub. Date: Jan. 25, 2024

(65) Prior Publication Data
US 2024/0418696 A1 Dec. 19, 2024

(51) Int. Cl.
*G01N 33/18* (2006.01)
*G06N 20/00* (2019.01)

(52) U.S. Cl.
CPC ......... *G01N 33/1833* (2013.01); *G06N 20/00* (2019.01)

(58) Field of Classification Search
CPC .... G01N 33/1833; G01N 33/00; G06N 20/00; E21B 2200/22; G06F 2113/08; G06F 30/27
See application file for complete search history.

(56) References Cited

U.S. PATENT DOCUMENTS 10,565,540 B2 2/2020 Webb et al.
2007/0239640 A1 10/2007 Coppola, Jr. et al.
(Continued)

FOREIGN PATENT DOCUMENTS

CN 106680446 A * 5/2017 ......... G01N 33/1813
CN 108150158 A * 6/2018 ......... E21B 49/0875
(Continued)

OTHER PUBLICATIONS

CN_106680446 Translation (Year: 2017).*
(Continued)

*Primary Examiner* — Manuel L Barbee
(74) *Attorney, Agent, or Firm* — Osha Bergman Watanabe & Burton LLP

(57) ABSTRACT

A method involving collecting a first geochemical data set for a first plurality of produced water samples; collecting a second plurality of produced water samples; performing geochemical analyses on the second plurality of produced water samples to form a second geochemical data set; and combining the first and second geochemical data sets into a database. The method further includes determining, by a subject matter expert, a water type for each produced water sample in the database and training a machine-learned model with the database to predict the water type of a produced water sample given its geochemical data. The method further includes collecting a third plurality of produced water samples, performing geochemical analysis on the third plurality of produced water samples, and determining, with the trained machine-learned model, the water type for each produced water sample in the third plurality of produced water samples using the third geochemical data set.

20 Claims, 15 Drawing Sheets

(56) References Cited

U.S. PATENT DOCUMENTS

| | | | |
|---|---|---|---|
| 2016/0377585 A1 | 12/2016 | El-Zefzafy et al. | |
| 2020/0184388 A1* | 6/2020 | Webb ................... | G06Q 10/063 |

FOREIGN PATENT DOCUMENTS

| | | |
|---|---|---|
| CN | 110689931 A | 1/2020 |
| CN | 111967576 A | 11/2020 |
| RU | 2123194 C1 | 12/1998 |

OTHER PUBLICATIONS

CN_108150158 Translation (Year: 2018).*

P. Birkle et al., "Machine Learning-based Approach for Automated Identification of Produced Water Types from Conventional and Unconventional Reservoirs", Fourth EAGE Conference on Petroleum Geostatistics, Sep. 2-6, 2019, Florence, Italy (5 pages).

Notification of Transmittal of the International Search Report and the Written Opinion of the International Searching Authiority issued in International Application No. PCT/RU 2022/000231 (9 pages).

M. A, Engle ety al., "Linking compositional data analysis with thermodynamic geochemical modeling: Oil fields brines from from the Permian Basin, USA", Journal of Geochemical Exploration, 2014, vol. 141, pp. 61-70 (10 pages).

H. Iwamori et al., "Classification of geochemical data based on multivariate statistical analyses: Complementary roles of cluster, principal component, and independent component analyses", AGU Publications, Geochemistry, Geophysics, Geosystems, 2017, pp. 994-101 (19 pages).

Y.K. Kharaka et al., "Deep Fluids in Sedimentary Basins", In: (eds: Holland, H.D. and Turekian, K.K., Treatise on Geochemistry, 2nd edn, vol. 7, pp. 472-515. Elsevier, Amsterdam, Netherlands (50 pages).

J. L. Shelton et al., "Machine learning can assign geological basin to produced water samples using major ion geochemistry", Natural Resources Research, vol. 30, No. 6, Dec. 2021, pp. 4147-4163 (17 pages).

* cited by examiner

202

| Water Types | | | | |
|---|---|---|---|---|
| Condensate Water | Formation Water | Supply Water | Brine | Mud Filtrate | Mixed |

| Produced Water Sample No. | Acidity (pH) | Ba [mg/L] | Cl [mg/L] | Geochemical Data | Na [mg/L] | TDS [mg/L] | Fe [mg/L] |
|---|---|---|---|---|---|---|---|
| 1 | 7.6 | 1 | 31962 | ⋯ | 15560 | 61790 | |
| 2 | 3.8 | 269 | 876 | ⋯ | 269 | 1723 | |
| ⋯ | ⋯ | ⋯ | ⋯ | ⋯ | ⋯ | ⋯ | ⋯ |
| I | 6.8 | 8 | 18169 | ⋯ | 10053 | 30860 | 19 |
| M-1 | 6.9 | 88 | 25122 | ⋯ | 18828 | 47492 | 21 |
| M | 6.6 | 98 | 28603 | ⋯ | 17675 | 49694 | 16 |

FIG. 2B

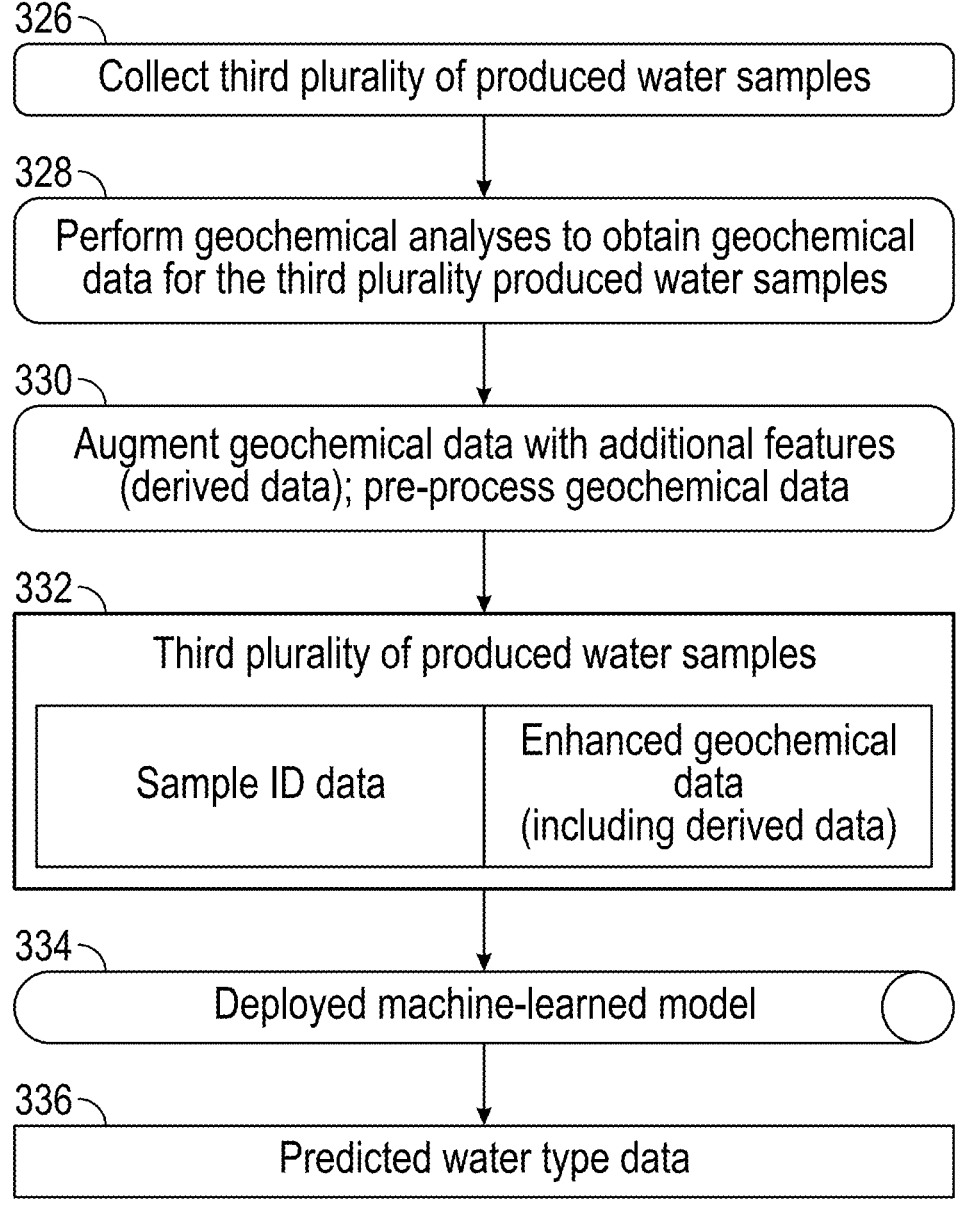

326

Collect third plurality of produced water samples

328

Perform geochemical analyses to obtain geochemical data for the third plurality produced water samples

330

Augment geochemical data with additional features (derived data); pre-process geochemical data

332

Third plurality of produced water samples

| Sample ID data | Enhanced geochemical data (including derived data) |

334

Deployed machine-learned model

336

Predicted water type data

FIG. 3B

| Model | Accuracy | Precision | Recall | F1 score |
|---|---|---|---|---|
| Random Forest | 0.94 | 0.94 | 0.95 | 0.94 |
| Support Vector Machine | 0.85 | 0.78 | 0.75 | 0.76 |
| K Nearest Neighbor | 0.8 | 0.61 | 0.6 | 0.58 |
| Extra Trees | 0.94 | 0.95 | 0.95 | 0.94 |
| Gradient Boosting Model (XGBoost) | 0.96 | 0.94 | 0.94 | 0.93 |
| Decision Tree | 0.91 | 0.84 | 0.87 | 0.85 |
| Multilayer Perceptron | 0.86 | 0.77 | 0.75 | 0.76 |

FIG. 5A

| | Brine (%) | Condensate Water (%) | Formation Water (%) | Mixed (%) | Mud Filtrate (%) | Supply Water (%) | True Label | Predicted Label |
|---|---|---|---|---|---|---|---|---|
| 1 | 77.13 | 3.12 | 5.47 | 5.02 | 6.36 | 2.91 | Brine | Brine |
| 2 | 78.15 | 3.08 | 5.42 | 4.98 | 5.49 | 2.88 | Brine | Brine |
| 3 | 4.62 | 3.08 | 78.82 | 4.91 | 5.72 | 2.86 | Formation Water | Formation Water |
| 4 | 5.81 | 3.69 | 28.48 | 52.34 | 6.46 | 3.23 | Mixed | Mixed |
| 5 | 4.84 | 3.23 | 5.64 | 5.15 | 78.13 | 3.02 | Mud Filtrate | Mud Filtrate |

FIG. 5B

| Metric | | | | |
|---|---|---|---|---|
| Method | Accuracy | Precision | Recall | F1-score |
| Self-training | 0.86 | 0.87 | 0.86 | 0.86 |
| Co-training | 0.8 | 0.79 | 0.78 | 0.8 |
| Cluster-then-label | 0.75 | 0.74 | 0.73 | 0.72 |
| Semi-Supervised SVM | 0.72 | 0.7 | 0.68 | 0.7 |

SOURCE DETERMINATION OF PRODUCED WATER FROM OILFIELDS WITH ARTIFICIAL INTELLIGENCE TECHNIQUES

BACKGROUND

The extraction of oil and gas from underground reservoirs is generally accompanied by water or brine, which is referred to as produced water. As reservoirs mature, especially if secondary or tertiary recovery methods are employed, the quantity of produced water typically increases and may often exceed the volume of extracted hydrocarbons before the reservoir is exhausted.

The produced water may originate from one or more sources, such as natural underground systems, drilling fluids, and fluids used in completion and workover activities. Natural sources may include groundwater from shallow aquifer systems or formation water from deeper water-leg or oil-leg horizons in and oil or gas reservoir. Generally, a drilling fluid is any fluid that is circulated in the borehole of a well to aid a drilling operation. Drilling fluids are commonly classified as oil-based mud (OBM), water-based mud (WBM), brine-based fluid, or synthetic-based fluid. The base component of water-based mud may be fresh water, seawater, brine, saturated brine, or a formate brine. Similarly, completion and workover fluids may be broadly categorized as dense salt solutions (completion brines), calcium carbonate weighting suspensions, and water-in-oil emulsions.

A precise characterization regarding the provenance of produced water, either from underground sources (e.g., formation water) or flowback from fluids associated with well activities (e.g., drilling fluid), is essential for strategic decisions during drilling and production operations. For example, regional salinity maps, and other subsurface models, may be generated, or at the very least informed, by tracking the origin of produced water and its associated geochemical composition.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

One or more embodiments disclosed herein generally relate to a method, including: collecting a first geochemical data set comprising geochemical data for a first plurality of produced water samples; collecting a second plurality of produced water samples from an oil and gas field; performing geochemical analyses on the second plurality of produced water samples to form a second geochemical data set, wherein the second geochemical data set comprises geochemical data for the second plurality of produced water samples; and combining the first geochemical data set and the second geochemical data set into a database. The method further includes determining, by a subject matter expert, a water type for each produced water sample in the database and training a machine-learned model on at least a portion of the database to predict the water type of a produced water sample given its geochemical data. The method further includes collecting a third plurality of produced water samples, performing geochemical analysis on the third plurality of produced water samples to form a third geochemical data set, wherein the third geochemical data set comprises geochemical data for the third plurality of produced water samples, and determining, with the trained machine-learned model, the water type for each produced water sample in the third plurality of produced water samples using the third geochemical data set.

One or more embodiments disclosed herein generally relate to a non-transitory computer readable medium storing instructions executable by a computer processor, the instruction including functionality for receiving a first geochemical data set comprising geochemical data for a first plurality of produced water samples, receiving a second plurality of produced water samples from an oil and gas field and a second geochemical data set, wherein the second geochemical data set comprises geochemical data for the second plurality of produced water samples, and combining the first geochemical data set and the second geochemical data set into a database. The instructions further include functionality for receiving a water type for each produced water sample in the database, wherein the water type is determined by a subject matter expert, and training a machine-learned model on at least a portion of the database to predict the water type of a produced water sample given its geochemical data. The instructions further include functionality for receiving a third plurality of produced water samples and a third geochemical data set, wherein the third geochemical data set comprises geochemical data for the third plurality of produced water samples, and determining, with the trained machine-learned model, the water type for each produced water sample in the third plurality of produced water samples using the third geochemical data set.

One or more embodiments disclosed herein generally relate to a system, the system including: a first geochemical data set comprising geochemical data for a first plurality of produced water samples; a second plurality of produced water samples from an oil and gas field; a second geochemical data set, wherein the second geochemical data set comprises geochemical data for the second plurality of produced water samples; a third plurality of produced water samples; a third geochemical data set, wherein the third geochemical data set comprises geochemical data for the third plurality of produced water samples; a plurality of water types, wherein the plurality of water types comprises a water type for each produced water sample in both the first and second pluralities of produced water samples, and wherein the water type for each produced water sample was determined by a subject matter expert; a trained machine-learned model; and a computer. The computer includes one or more computer processors, and a non-transitory computer readable medium storing instructions executable by a computer processor. The instructions include functionality for processing, with the trained machine-learned model, the third geochemical data set to determine a water type for each produced water sample in the third plurality of produced water samples.

Other aspects and advantages of the claimed subject matter will be apparent from the following description and the appended claims.

BRIEF DESCRIPTION OF DRAWINGS

FIG. 2A depicts water types, in accordance with one or more embodiments.

FIG. 2B depicts example geochemical data for a plurality of produced water samples, in accordance with one or more embodiments.

FIGS. 3A-1 and 3A-2 depicts a flowchart, in accordance with one or more embodiments.

FIG. 3B depicts a flowchart, in accordance with one or more embodiments.

FIG. 5A depicts predicted water types, determined by a machine-learned model, for a plurality of produced water samples, in accordance with one or more embodiments.

FIG. 5B depicts a confusion matrix, in accordance with one or more embodiments.

DETAILED DESCRIPTION

Figure 1:
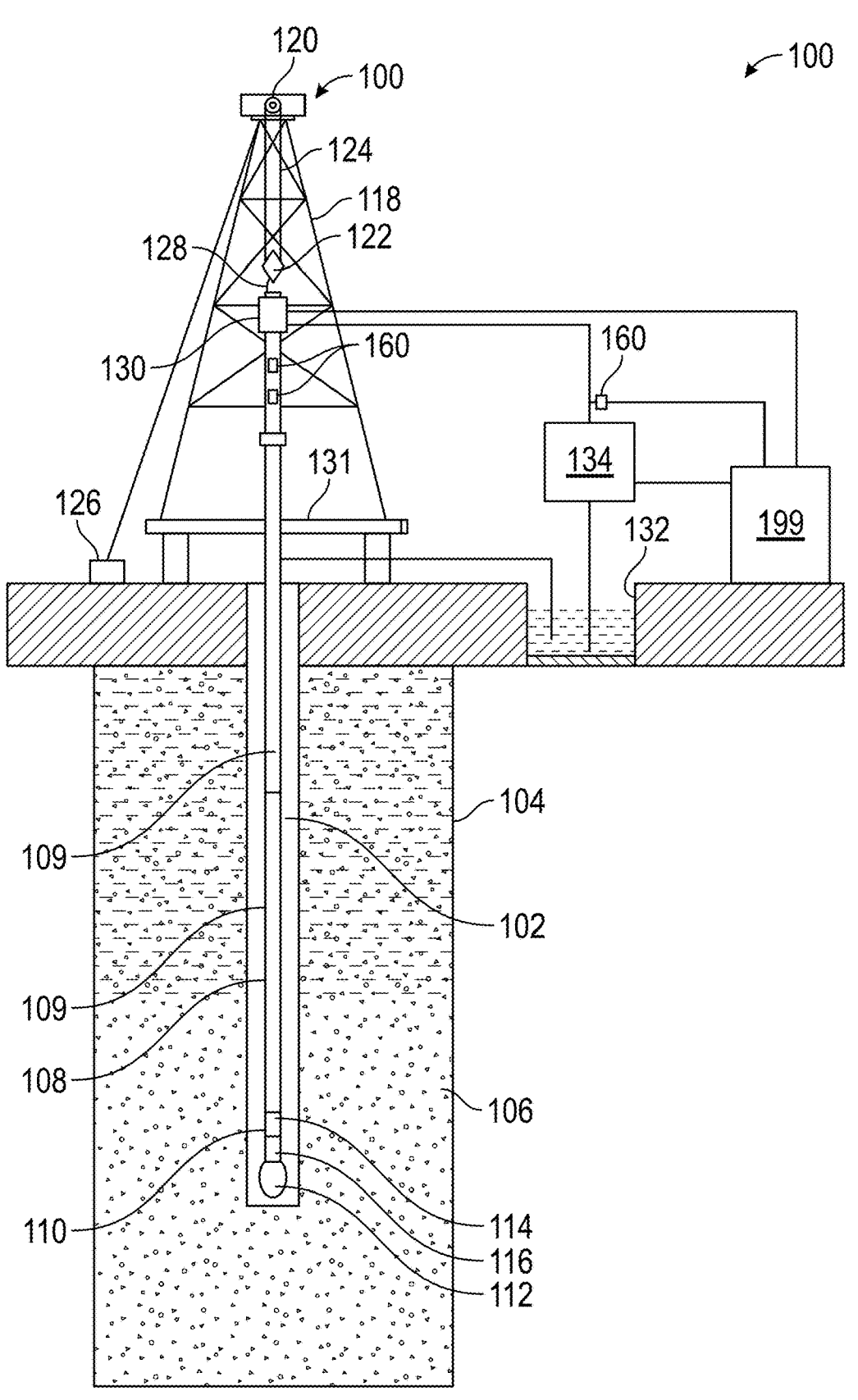
FIG. 1 depicts a well system, in accordance with one or more embodiments.

FIG. 1 illustrates an example well site (100). A well site (100) may be used to extract oil and gas, generally referred to as hydrocarbons, from underground reservoirs. In general, well sites may be configured in a myriad of ways. Therefore, well site (100) is not intended to be limiting with respect to the particular configuration of the drilling equipment. The well site (100) is depicted as being on land. In other examples, the well site (100) may be offshore, and drilling may be carried out with or without use of a marine riser. A drilling operation at well site (100) may include drilling a wellbore (102) into a subsurface including various formations (104, 106). For the purpose of drilling a new section of wellbore (102), a drill string (108) is suspended within the wellbore (102).

The drill string (108) may include one or more drill pipes (109) connected to form conduit and a bottom hole assembly (BHA) (110) disposed at the distal end of the conduit. The BHA (110) may include a drill bit (112) to cut into the subsurface rock. The BHA (110) may include measurement tools (114), such as a measurement-while-drilling (MWD) tool and logging-while-drilling (LWD) tool. Measurement tools (114) may include sensors and hardware to measure downhole drilling parameters, and these measurements may be transmitted to the surface using any suitable telemetry system known in the art. The BHA (110) and the drill string (108) may include other drilling tools known in the art but not specifically shown.

The drill string (108) may be suspended in wellbore (102) by a derrick (118). A crown block (120) may be mounted at the top of the derrick (118), and a traveling block (122) may hang down from the crown block (120) by means of a cable or drilling line (124). One end of the cable (124) may be connected to a drawworks (126), which is a reeling device that may be used to adjust the length of the cable (124) so that the traveling block (122) may move up or down the derrick (118). The traveling block (122) may include a hook (128) on which a top drive (130) is supported.

The top drive (130) is coupled to the top of the drill string (108) and is operable to rotate the drill string (108). Alternatively, the drill string (108) may be rotated by means of a rotary table (not shown) on the drilling floor (131). Drilling fluid (commonly called "mud") may be stored in a mud pit (132), and at least one pump (134) may pump the mud from the mud pit (132) into the drill string (108). The mud may flow into the drill string (108) through appropriate flow paths in the top drive (130) (or a rotary swivel if a rotary table is used instead of a top drive to rotate the drill string (108)). Drilling fluid (or mud) is any fluid that is circulated in the wellbore (102) to aid in the drilling operation. Drilling fluids may be broadly categorized according to their principal constituent. For example, a drilling fluid may be said to be an oil-based mud (OBM), water-based mud (WBM), brine-based fluid, or synthetic-based fluid. The base component for a water-based drilling fluid (or WBM) may be fresh water, seawater, brine, saturated brine, or a formate brine. The liquid part of a drilling fluid is known as "mud filtrate." When a drilling fluid passes through a porous medium (e.g., subsurface formations (104, 106)), solid particulates suspended in the drilling fluid may become separated from the mud filtrate. Solid particulates, upon separation, may accumulate and form a layer commonly known as "mudcake." Some well sites (100) may include an automated drilling fluid property system (not shown). An automated drilling fluid property system may include hardware and/or software with functionality for automatically supplying and/or mixing weighting agents, buffering agents, rheological modifiers, and/or other additives to the drilling fluid until it matches and/or satisfies one or more desired drilling fluid properties. Examples of weighting agents may include barite, hematite, calcium carbonate, siderite, etc. A buffering agent may be a pH buffering agent that causes a drilling fluid mixture to resist changes in pH levels. For example, a buffering agent may include water, a weak acid (or weak base) and salt of the weak acid (or a salt of weak base). Rheological modifiers may include drilling fluid additives that adjust one or more flow properties of a drilling fluid. In summary, the composition of a drilling fluid may be complex and a drilling fluid may be tailored to a specific well site (100), and, in some instances, the composition of a drilling fluid may be altered in real-time according to the needs of a drilling operation.

In one implementation, a system (199) may be disposed at or communicate with the well site (100). System (199) may control at least a portion of a drilling operation at the well site (100) by providing controls to various components of the drilling operation. In one or more embodiments, system (199) may receive data from one or more sensors (160) arranged to measure controllable parameters of the drilling operation. As a non-limiting example, sensors (160) may be arranged to measure: weight on bit (WOB), drill string rotational speed (RPM), flow rate of the mud pumps (GPM), and rate of penetration of the drilling operation (ROP). In one or more embodiments, the drilling operation may be controlled by the system (199).

Sensors (160) may be positioned to measure parameter(s) related to the rotation of the drill string (108), parameter(s) related to travel of the traveling block (122), which may be used to determine ROP of the drilling operation, and parameter(s) related to flow rate of the pump (134). For illustration purposes, sensors (160) are shown on drill string (108) and proximate mud pump (134). The illustrated locations of sensors (160) are not intended to be limiting, and sensors (160) could be disposed wherever drilling parameters need to be measured. Moreover, there may be many more sensors (160) than shown in FIG. 1 to measure various other parameters of the drilling operation. Each sensor (160) may be configured to measure a desired physical stimulus.

During a drilling operation at the well site (100), the drill string (108) is rotated relative to the wellbore (102), and weight is applied to the drill bit (112) to enable the drill bit (112) to break rock as the drill string (108) is rotated. In some cases, the drill bit (112) may be rotated independently with a drilling motor. In some implementations, the drilling motor is a positive displacement motor (116) located on the distal end of the drill string (108) as part of the BHA (110). In further embodiments, the drill bit (112) may be rotated using a combination of the drilling motor, such as a positive displacement motor (116), and the top drive (130) (or a rotary swivel if a rotary table is used instead of a top drive to rotate the drill string (108)). While cutting rock with the drill bit (112), mud is pumped into the drill string (108).

The drilling fluid flows down the drill string (108) and exits into the bottom of the wellbore (102) through nozzles in the drill bit (112). The drilling fluid in the wellbore (102) then flows back up to the surface in an annular space between the drill string (108) and the wellbore (102) with entrained cuttings.

The drilling fluid with the cuttings is returned to the pit (132) to be circulated back again into the drill string (108). Typically, the cuttings are removed from the drilling, and the drilling fluid is reconditioned as necessary, before pumping the drilling fluid again into the drill string (108).

Depending on the depth of hydrocarbon bearing formation and other geological complexes, a well can have several hole sizes before it reaches its target depth. A steel pipe, or casing (not shown), may be lowered in each hole and a cement slurry may be pumped from the bottom up through the presumably annular space between the casing and the wellbore (102) to fix the casing, seal the wellbore from the surrounding subsurface (104, 106) formations, and ensure proper well integrity throughout the lifecycle of the well. The casing may be inserted periodically while drilling out the well.

Upon finishing drilling the wellbore (102), the well may undergo a "completions" process to stabilize the well and provide reliable access to the desired hydrocarbons. In some implementations, the final wellbore (102) can be completed using either cased and cemented pipe, which is later perforated to access the hydrocarbon, or it may be completed using a multi-stage open-hole packer assembly. During completions, additional fluids may be used or injected into the well. Completion fluids may be generally categorized as dense salt solutions (completion brines), calcium carbonate weighting suspensions, and water-in-oil emulsions. Completion brines are typically highly concentrated solutions of inorganic salts, mostly chlorides and bromides. Throughout the lifecycle of a well, repair or stimulation activities may be performed to restore, prolong, or enhance the production of hydrocarbons from a reservoir. These activities may be collectively referred to as workover activities, or simply workover. Workover activities may involve the use of fluids. Workover fluids may be similar to drilling fluids or completion fluids (e.g., dense salt solutions).

Once completed, a well site (100) may be used in production to extract hydrocarbons from underground reservoirs. The produced hydrocarbons are often accompanied by water or brine, which is referred to as produced water. As reservoirs mature, especially if secondary or tertiary recovery methods are employed, the quantity of produced water typically increases and may often exceed the volume of extracted hydrocarbons before the reservoir is exhausted.

The produced water may originate from one or more sources, such as natural underground systems, drilling fluids, and fluids used in completion and workover activities. That is, fluids used during drilling, completion, or workover of a well site (100) may return during production. Natural sources may include groundwater from shallow aquifer systems or formation water from deeper water-leg or oil-leg horizons in an oil or gas reservoir. The geochemical composition of produced water is dependent on its origin. In greater detail, geochemical characteristics of produced water depend on the geographic location of the well site (100), the subsurface formations (104, 106) and lithology, the type of fluids used during drilling, completion, and workover, and the composition, quantity, and proximity of naturally occurring groundwater. Because the geochemical characteristics of produced water depend on the origin of the produced water, analysis of samples of produced water can reveal key information about the underground system. For example, analysis of produced water throughout the life of the well may be used to determine, or at least estimate, fluid migration and reservoir compartmentalization. Further, identification of the origin of produced water may inform subsurface models such as regional salinity maps. Consequently, the determination of the provenance of produced water, either from underground sources (e.g., formation water) or flowback from fluids associated with well activities (e.g., drilling fluid), is essential for strategic decisions during drilling and production operations.

Generally, produced water may be sampled from a well site (100). Further, produced water may be sampled from a well site (100) periodically over the lifetime of a well such that the produced water samples may form a time history of the produced water content. In practice, most recovered produced water samples are composed of mixtures of natural fluids from deep groundwater systems (i.e., formation water) and artificial fluids from well site (100) operations. As previously described, examples of artificial fluids include drilling fluid and fluids used during completion and workover activities. Due to the complexity of the composition of many artificial fluids, and the fact that produced water is often a mixture of fluids of various origins, the identification of the origin of a produced water sample is generally a difficult task.

Current attempts to assess the origin of produced water include analysis of chloride and salinity concentrations of produced water samples. This method aims to classify produced water as originating from natural sources or as an artificial fluid. While simple, this method is associated with high uncertainty and is often unreliable or inaccurate. This is because naturally occurring water sources and artificial fluids may have overlapping ranges of chloride and salinity concentrations. For example, the salinity of pore water in sedimentary basins can range from 5,000 mg/L to 300,000 mg/L (See Kharaka, Y. K., & Hanor, J. S. (2014). Deep Fluids in Sedimentary Basins.). Further, the heterogeneous composition of each single fluid type, as well as mixing processes between different fluid types (i.e., formation water with mud filtrate), make a precise fluid identification difficult. The classification of produced water samples by drilling or operational staff by chloride analysis in the field or professional experience must therefore be declared as a qualitative approach with a low probability of correctness. As such, chloride and salinity concentrations cannot be utilized as indicative and exclusive parameters for produced water classification. More complex methods include using logging tools, such as 2D NRM, NRM antenna gain, NMR antenna "Q" factor, and neutron-gamma spectroscopy, to form an indirect indication of the salinity, or brine concentration in a reservoir. However, a major disadvantage of these methods is that they are costly and cannot differentiate produced water samples with mixed content or inflow from one or more sources.

In one aspect, embodiments disclosed herein relate to classifying produced water according to an origin through the statistical assessment of geochemical data describing the produced water. Geochemical data may include the measured concentrations of elements in a sample of produced water. In accordance with one or more embodiments, the geochemical data associated with a sample of produced water are processed with a machine-learned model. The machine-learned model may assign a class to the produced water sample or output a probability that the produced water sample belongs to a given class.

Herein, class labels are directed toward water types. FIG. 2A depicts various water types (202), such as: condensate water, formation water, supply water, brine, mud filtrate, and mixed. FIG. 2B illustrates example geochemical data (204) for M number of produced water samples. As seen, geochemical data (204) may include, but are not limited to, chemical and physical parameters (e.g., density, pH) and elemental or molecular concentrations (e.g., milligrams per liter of Na, milligrams per liter of $HCO_3$, etc.) for each produced water sample. Therefore, in accordance with one or more embodiments, a machine-learned model is developed such that it may receive a geochemical description for a produced water sample and return its water type (202).

Machine learning (ML), broadly defined, is the extraction of patterns and insights from data. The phrases "artificial intelligence", "machine learning", "deep learning", and "pattern recognition" are often convoluted, interchanged, and used synonymously throughout the literature. This ambiguity arises because the field of "extracting patterns and insights from data" was developed simultaneously and disjointedly among a number of classical arts like mathematics, statistics, and computer science. For consistency, the term machine learning (ML), or machine-learned, will be adopted herein, however, one skilled in the art will recognize that the concepts and methods detailed hereafter are not limited by this choice of nomenclature.

Machine-learned model types may include, but are not limited to, k-means, k-nearest neighbors, neural networks, logistic regression, random forests, generalized linear models, and Bayesian regression. Also, machine-learning encompasses model types that may further be categorized as "supervised", "unsupervised", "semi-supervised", or "reinforcement" models. One with ordinary skill in the art will appreciate that additional or alternate machine-learned model categorizations may be defined without departing form the scope of this disclosure. Machine-learned model types are usually associated with additional "hyperparameters" which further describe the model. For example, hyperparameters providing further detail about a neural network may include, but are not limited to, the number of layers in the neural network, choice of activation functions, inclusion of batch normalization layers, and regularization strength. Commonly, in the literature, the selection of hyperparameters surrounding a model is referred to as selecting the model "architecture". Greater detail regarding the machine-learned models, in accordance with one or more embodiments, will be provided below in the present disclosure.

Figures 1, 3A:
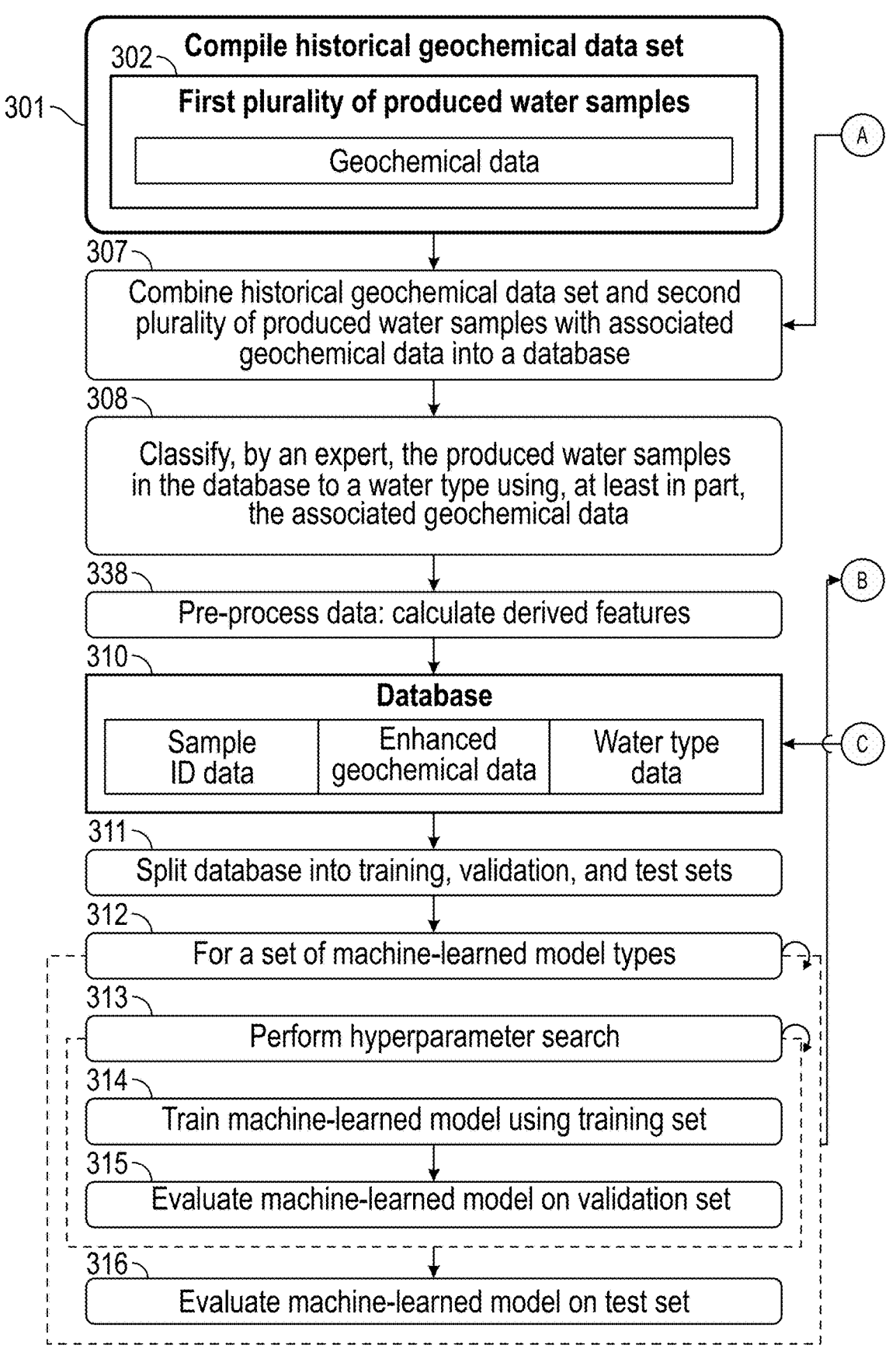
Figures 2, 3A:
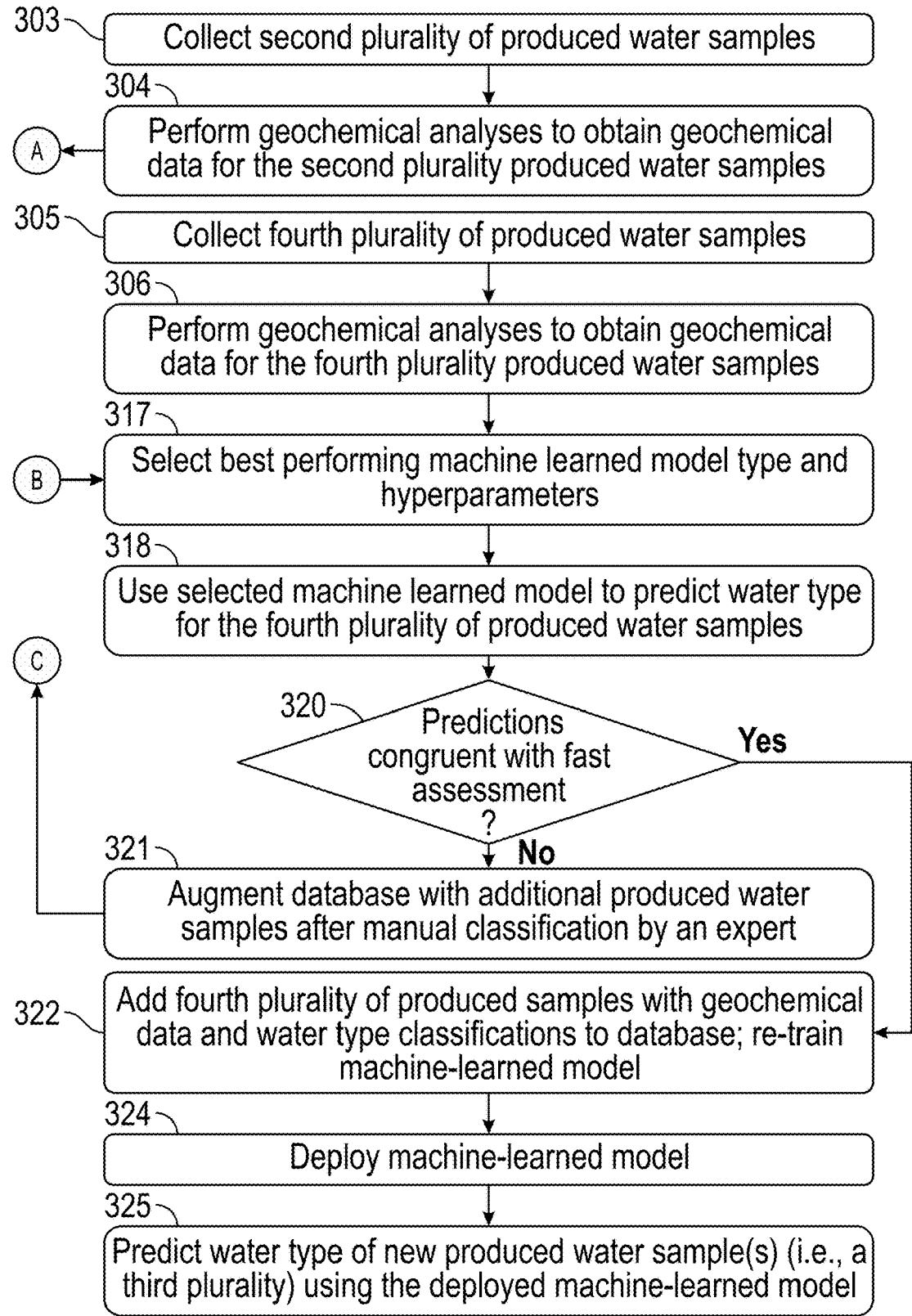

In accordance with one or more embodiments, FIG. 3A depicts a flowchart which describes in greater detail the process of developing and using a machine-learned model to classify, or otherwise determine, the water type of a sample of produced water. As seen, in Block 301, a historical geochemical data set is compiled. The historical geochemical data set contains geochemical data (204), like that shown in FIG. 2B, for a first plurality of produced water samples (302). In Block 303, a second plurality of produced water samples are collected. To obtain geochemical data for the second plurality of produced water, a geochemical analysis is performed on each produced water sample in the second plurality of produced water samples, as shown in Block 304. The result of Block 304 is geochemical data for the second plurality of produced water samples. For example, in accordance with one or more embodiments, the geochemical data includes measured quantities for pH, density, total dissolved salinity (TDS), and concentrations of Na, Ca, Mg, K, Cl, $HCO_3$, $CO_3$, $SO_4$, Ba, and Sr, for each produced water sample.

In Block 307, the second plurality of produced water samples, with associated geochemical data, and the first plurality of produced water samples (from the historical geochemical data set), with associated geochemical data, are combined into a database (310). Each produced water sample in the database is classified, by an expert, to a water type, as seen in Block 308. To make the determination, the expert uses, at least, the associated geochemical data of each produced water sample. In the present disclosure, the expert may classify a produced water sample as either brine, condensate water, formation water, mixed, mud filtrate, or supply water. In Block 338, the geochemical data is preprocessed. Typical pre-processing methods may include removal of outliers and/or low-quality data, imputation, etc. In some embodiments, no pre-processing is performed such that the geochemical data continues unaltered. One with ordinary skill in the art will recognize that nearly any pre-processing technique known in the art may be applied, such that the fact that all pre-processing techniques are not enumerated herein does not impose a limitation on the present disclosure. Additionally, as shown in Block 338, the geochemical data may be combined or functionally altered to produce derived features. The derived features, if any, are added to the geochemical data and the geochemical data is considered to be enhanced. In accordance with one or more embodiments, the following ratios are calculated as derived features: specific gravity, Ca/K, Cl/K, $SO_4$/Ba, Sr/K, Sr/Ba, Na/Ba, $HCO_3$/Na, Cl/$SO_4$, Cl/Sr, Ca/Sr, Ca/$HCO_3$, Cl/$HCO_3$, K/Ba, Ca/Na, $SO_4$, K/Sr, $HCO_3$, Ca/$SO_4$, Ba/Ca, Br/Ca, Br/Mg, Ba/Sr, Cl/Na, $HCO_3$/Br, Sr/Mg, Mg/K, K/Mg, K/$HCO_3$, Ca/Cl, Na/$SO_4$, Cl/Mg, Na/Sr, and Ba/K. As such, the database (310) includes sample ID data, or a mechanism to identify produced water samples (i.e., each produced water sample has a unique identifier), enhanced geochemical data (i.e., a geochemical description of each produced water sample which may have undergone pre-processing and may include derived features), and water type data (i.e., the water type of each produced water sample as assigned by an expert).

To effectively train a machine-learned model, the database (310) is split into three distinct sets; namely, a training set, a validation set, and a test set, as shown in Block 311. A common splitting method is to randomly select a portion X of the produced water samples for the training set, a portion Y for the validation set, and assign the remaining portion of samples to the test set. For example, 80% of the produced water samples may be assigned to the training set, 10% to the validation set, and the remaining 10% to the testing set. However, one with ordinary skill in the art will recognized that other splitting methods and/or set proportions may be used without exceeding the scope of this disclosure. In some embodiments, a validation set is not used such that the data is only split into training and test sets.

Once the database (310) is split, the training set, validation set, and test set are used to train, tune, evaluate, and select a machine-learned model. In accordance with one or more embodiments, to discover a high performing machine-learning model, one or more machine-learned model types and associated model hyperparameters are tested. To do so, a set of machine-learned model types may be defined. For example, a set may be defined to contain the model types: {logistic regression, k-nearest neighbors, gradient boosting, neural network}. Block 312 represents an iterator where each model type in the set of model types is processed according to the enclosed blocks. Likewise, Block 313 represents another iterator to cycle over hyperparameters associated with the model and perform the enclosed operations. In other words, in Block 312, a model type is selected and in Block 313 associated hyperparameters are selected. The hyperparameter search may be performed using any method known in the art. As non-limiting examples, the hyperparameters search of Block 313 may be performed according to a grid search, a random search, a genetic algorithm search, or a Bayesian-based search.

For each model type and applied hyperparameters, the machine-learned model is trained using the training set, as shown in Block 314. Once a machine-learned model is trained, its performance is evaluated on the validation set, as depicted in Block 315. In the case where there is no validation set, such as when the database is only split into training and testing sets, the testing set may be used for the validation set. In some embodiments, one or more validation sets may be temporarily extracted from the training set using methods like cross-validation (e.g., leave-one-out cross-validation, k-folds cross-validation). Evaluating the machine-learned model consists of processing the enhanced geochemical data of the validation set with the trained machine-learned model to produce water type predictions, and comparing the predicted water types with the actual (or known) water types. The machine-learned model may only predict water types congruent with the set of water types assigned by the expert. That is, the machine-learned model may predict that a produced water sample is either brine, condensate water, formation water, mixed, mud filtrate, or supply water. In some embodiments, the machine-learned model may predict the probability that a produced water sample belongs to a specified water type. The comparison is done using a comparison function which quantifies the difference between the predicted water types and actual water types over the validation set. In accordance with one or more embodiments, the comparison function is the cross-entropy function, however, one with ordinary skill in the art will appreciate that other comparison functions may be employed without departing from the scope of the disclosure. The evaluation of the validation set in Block 315 guides the hyperparameter search of Block 313. That is, for each model type, the best combination of hyperparameters is selected by comparing the performance of each model, with its associated hyperparameters, as evaluated on the validation set. As stated, in some embodiments, the hyperparameter search may be performed over data sets temporarily extracted from the training data through cross-validation techniques.

In Block 316, each machine-learned model type, with its associated best set of hyperparameters, is evaluated using the test set. Like before, the evaluation is done using a comparison function, such as the cross-entropy function, to quantify the difference between the model-predicted water types and the actual water types over the test set. Through the iterators of Blocks 312 and 313, and the evaluations of Blocks 315 and 316, the best performing machine-learned model type, and associated hyperparameters, may be identified. In Block 317, this best performing machine-learned model is selected.

Keeping with FIG. 3A, in Block 305, a fourth plurality of produced water samples is collected. The fourth plurality of produced water samples is processed through a geochemical analysis to obtain geochemical data for the fourth plurality of produced water samples, as depicted in Block 306. The geochemical data for the fourth plurality of produced water samples undergoes the same pre-processing, if any, and derived feature calculations, if any, of Block 338.

In Block 318, the enhanced geochemical data for the fourth plurality of produced water samples is processed with the selected machine-learned model of Block 317. The selected machine-learned model predicts a water type for each produced water sample in the fourth plurality of produced water samples. In Block 320, the water type predictions for the fourth plurality of produced water samples undergo a fast assessment. In the fast assessment, a subject matter expert evaluates the water type predictions for obvious inaccuracies. While care is taken during the fast assessment to determine if the selected machine-learned model is accurately classifying new produced water samples (samples previously unseen by the machine-learned model during training, validation, and testing procedures), the fast assessment is not as time-consuming as the expert classification step of Block 308. are compared to the expert classifications. If the selected machine-learned model fails to accurately predict the water type for the fourth plurality of produced water samples, as determined during the fast assessment, then it is indicative that the database (310) requires more produced water samples in order to adequately develop a machine-learned model. In this case, as depicted in Block 321, the database (310) is augmented with additional produced water samples, for example, by obtaining more historical geochemical data. It should be noted that the augmented produced water samples are classified by an expert and any pre-processing steps and derived feature calculations are performed before adding the additional samples to the database. Once the database has been augmented with the additional produced water samples, the process of developing a machine-learned model is continues, anew, at Block 311. When augmenting the database with additional data, it is preferable to obtain produced water samples with the same water type as those which were misclassified when evaluating the selected machine-learned model in Blocks 318 and 320. The process of obtaining more produced water samples and associated geochemical data, augmenting the database (310), and training, evaluating, and selecting a machine-learned model is repeated until the selected machine-learned model can accurately predict the water types of the fourth plurality of produced water samples (Block 320). When the selected machine-learned model accurately predicts the water types of the fourth plurality of produced water samples, the fourth plurality of produced water samples is added, with associated enhanced geochemical data and water type classifications, to the database (310). Then, the selected model, with associated hyperparameters, is re-trained, without performing model type and hyperparameter searches, as depicted in Block 322. In Block 324, the model is deployed. Deploying the model consists of making the model readily accessible to be used with new produced water samples, for which enhanced geochemical data exists, but the produced water samples do not have water types determined by an expert. For example, a third plurality of produced water samples may be collected. Geochemical analyses may be performed on the third plurality of produced water samples such that there is geochemical data for the third plurality of produced water samples. The geochemical data of the third plurality of produced water samples will undergo the same pre-processing steps and derived feature steps, if any, as defined in Block 338. Thus, the enhanced geochemical data of the third plurality of produced water samples may be processed by the deployed machine-learned model. That is, the deployed machine-learned model determines the water type for a produced water sample given its enhanced geochemical data (e.g., a sample from the third plurality of produced water samples), as shown in Block 325.

FIG. 3B depicts, in greater detail, the use of the deployed machine-learned model (334). To use the deployed machine-learned model, first, new produced water samples are collected. To reduce ambiguity, the new produced water samples are referenced as a third plurality of produced water samples, as shown in Block 326. In Block 328, geochemical analysis is performed on the third plurality of produced water samples such that geochemical data exists for each produced water sample. In Block 330, the geochemical data for the third plurality of produced water samples are pre-processed and augmented with derived features. The pre-processing method applied, if any, and the calculation of derived features, if any, are identical to those used during model development (FIG. 3A). To be explicit, the data associated with the third plurality of produced water samples is depicted in Block 332. As shown, the third plurality of produced water samples, after geochemical analysis, pre-processing, and augmentation, consists of an identifier and enhanced geochemical data for each produced water sample in the plurality. The enhanced geochemical data for the third plurality of produced water samples is processed by the deployed machine learned model (334), which predicts the water type of each sample. That is, the output of the deployed machine-learned model (334) is predicted water type data (336) for the third plurality of produced water samples.

As previously stated, many machine-learned model types may be employed in the framework depicted in FIGS. 3A and 3B. For example, machine-learned model types may include, but are not limited to, random forest, support vector machine, k-nearest neighbors, k-means, extra trees, and neural networks. Further, depending on the machine-learned model type, the machine-learning method may be "supervised", "unsupervised", or "semi-supervised". In some embodiments, the selected machine-learned model type is a gradient boosted trees classifier. Generally, a gradient boosted trees classifier is an ensemble of decision trees.

A decision tree is composed of nodes. A decision is made at each node such that data present at the node are segmented. Typically, at each node, the data at said node, are split into two parts, or segmented bimodally, however, multimodal segmentation is possible. The segmented data can be considered another node and may be further segmented. As such, a decision tree represents a sequence of segmentation rules. The segmentation rule (or decision) at each node is determined by an evaluation process. The evaluation process usually involves calculating which segmentation scheme results in the greatest homogeneity or reduction in variance in the segmented data. However, a detailed description of this evaluation process, or other potential segmentation scheme selection methods, is omitted for brevity and does not limit the scope of the present disclosure.

Further, if at a node in a decision tree, the data are no longer to be segmented, that node is said to be a "leaf node". Commonly, values of data found within a leaf node are aggregated, or further modeled, such as by a linear model, so that a leaf node represents a class. The class of a leaf node will hereinafter be referred to as the assigned class of the leaf node. A decision tree can be configured in a variety of ways, such as, but not limited to, choosing the segmentation scheme evaluation process, limiting the number of segmentations, and limiting the number of leaf nodes. Generally, when the number of segmentations or leaf nodes in a decision tree is limited, the decision tree is said to be a "weak learner."

In most implementations, the decision trees from which a gradient boosted trees classifier is composed are weak learners. Additionally, for a gradient boosted trees classifier, the decision trees are ensembled in series, wherein each decision tree makes a weighted adjustment to the output of the preceding decision trees in the series. The process of ensembling decision trees in series, and making weighted adjustments, to form a gradient boosted trees classifier is best illustrated by considering the training process of a gradient boosted trees classifier.

The following description of the gradient boosted trees training process assumes that properly formatted training data (after normalization, imputation, etc.), which contains both the data inputs (enhanced geochemical data) and the desired output data (or target data, or "targets") (water types), are supplied.

Training a gradient boosted trees classifier consists of the selection of segmentation rules for each node in each decision tree; that is, training each decision tree. Once trained, a decision tree is capable of processing data. For example, a decision tree may receive a data input. The data input is sequentially transferred to nodes within the decision tree according to the segmentation rules of the decision tree. Once the data input is transferred to a leaf node, the decision tree outputs the assigned class of the associated leaf node.

Generally, training a gradient boosted classifier firstly consists of making a simple prediction (SP) for the target data. The simple prediction (SP) may the most frequent class of the target data, or the log odds or cross-entropy of the frequency of classes in the target data. The simple prediction (SP) is subtracted from the targets to form a first residuals. The first decision tree in the series is created and trained, wherein the first decision tree attempts to predict the first residuals forming first residual predictions. The first residual predictions from the first decision tree are scaled by a scaling parameter. In the context of gradient boosted trees the scaling parameter is known as the "learning rate" ($\eta$). The learning rate is one of the hyperparameters governing the behavior of the gradient boosted trees regressor. The learning rate ($\eta$) may be fixed for all decision trees or may be variable or adaptive. The first residual predictions of the first decision tree are multiplied by the learning rate ($\eta$) and added to the simple prediction (SP) to form a first predictions. The first predictions are subtracted from the targets to form a second residuals. A second decision tree is created and trained using the data inputs and the second residuals as targets such that it produces second residual predictions. The second residual predictions are multiplied by the learning rate ($\eta$) and are added to the first predictions forming second predictions. This process is repeated recursively until a termination criterion is achieved.

Many termination criteria exist and are not all enumerated here for brevity. Common termination criteria are terminating training when a pre-defined number of decision trees has been reached, or when improvement in the residuals is no longer observed.

Once trained, a gradient boosted trees classifier may make predictions using input data. To do so, the input data is passed to each decision tree, which will form a plurality of residual predictions. The plurality of residual predictions is multiplied by the learning rate ($\eta$), summed across every decision tree, and added to the simple prediction (SP) formed during training to produce the gradient boosted trees predictions. In some instances, a conversion is required to convert the output of the gradient boosted trees prediction to a class assignation.

One with ordinary skill in the art will appreciate that many adaptions may be made to gradient boosted trees and that these adaptions do not exceed the scope of this disclosure. Some adaptions may be algorithmic optimizations, efficient handling of sparse data, use of out-of-core computing, and parallelization for distributed computing. In accordance with one or more embodiments, the selected machine-learned model type is an adapted gradient boosted trees model known as XGBoost.

Figure 4:
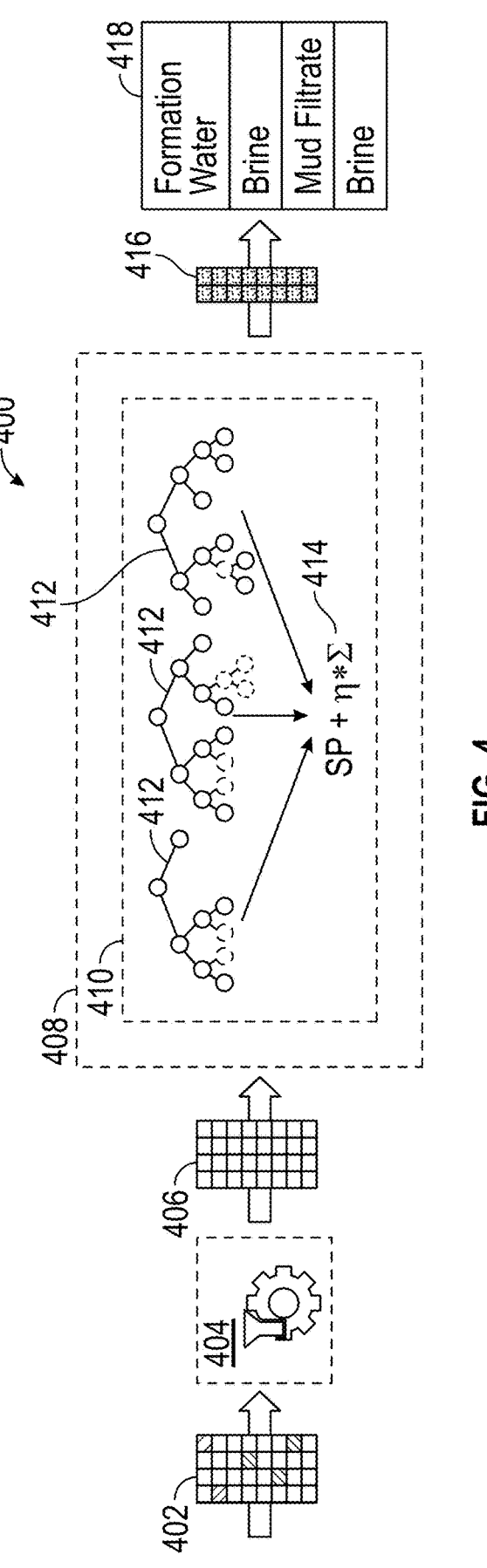
FIG. 4 depicts a system, in accordance with one or more embodiments.

FIG. 4 depicts, generally, the flow of data through a trained gradient boosted trees classifier in accordance with one or more embodiments. As seen, input data (402) is received. The input data is geochemical data for each produced water sample to be processed by the gradient boosted trees classifier. The input data (402) is pre-processed (404) as previously described. The result of the pre-processing (404) is pre-processed data (406) (e.g., normalized), augmented with derived features. In the context of the current disclosure, the pre-processed data (406) is enhanced geochemical data.

The pre-processed data (406) is passed to a machine-learned model (408). In FIG. 4, the machine-learned model (408) is further represented as a gradient boosted trees classifier (410) composed of a plurality of decision trees (412). As such, the pre-processed data (406) is processed by each decision tree (412) and the output of each decision tree is collected, multiplied by the learning rate ($\eta$), summed, and added to the simple prediction (SP) established during training forming an ensemble (414). The result of the ensemble (414) is returned as the machine-learned model prediction (416). Depending on the configuration of the gradient boosted trees classifier (410), the model prediction (416) may take various forms. For example, the model prediction (416) may return a probability that a produced water sample belongs to a given water type. In any case, the model prediction (416) may be directly converted to a predicted water type (418), for example, by selecting the water type with the highest predicted probability.

As a concrete example, the workflow of FIG. 3 was partially applied to a dataset of 206 produced water samples (i.e., Block 303 of FIG. 3). A geochemical analysis was performed on the 206 produced water samples to obtain geochemical data for the samples and each sample was classified by an expert (Blocks 304 and 308). The 206 produced water samples did not undergo pre-processing but the derived features were calculated (Block 338) as previously described. The 206 produced water samples, with associated enhanced geochemical data and expert-determined water types, were arbitrarily split into a training set containing 182 of the samples and a test set containing the remaining 24 samples (Block 311). Various supervised and semi-supervised methods were iterated through according to Block 312 of FIG. 3. Specifically, the set of machine-learned model types was {random forest, support vector machine, k-nearest neighbors, extra trees, gradient boosting classifier (XGBoost), decision tree, multilayer perceptron}. A grid search was performed to discover the best combination of hyperparameters for each machine-learned model type (Block 313). For training (Block 314) and model evaluation (Block 315), a 5-fold cross-validation technique was employed such that a dedicated validation set was not required. Various performance metrics were used to evaluate the best machine-learned model for each machine-learned type using the test set (Block 316). The results of the evaluation metrics for each machine-learned model type are shown in FIG. 5A. As seen in FIG. 5A, of the machine-learned model types evaluated, the random forest, XGBoost (implementation of a gradient boosted classifier), and extra trees demonstrated the best performance across the metrics of accuracy, precision, recall, and F1-score.

Figure 5C:
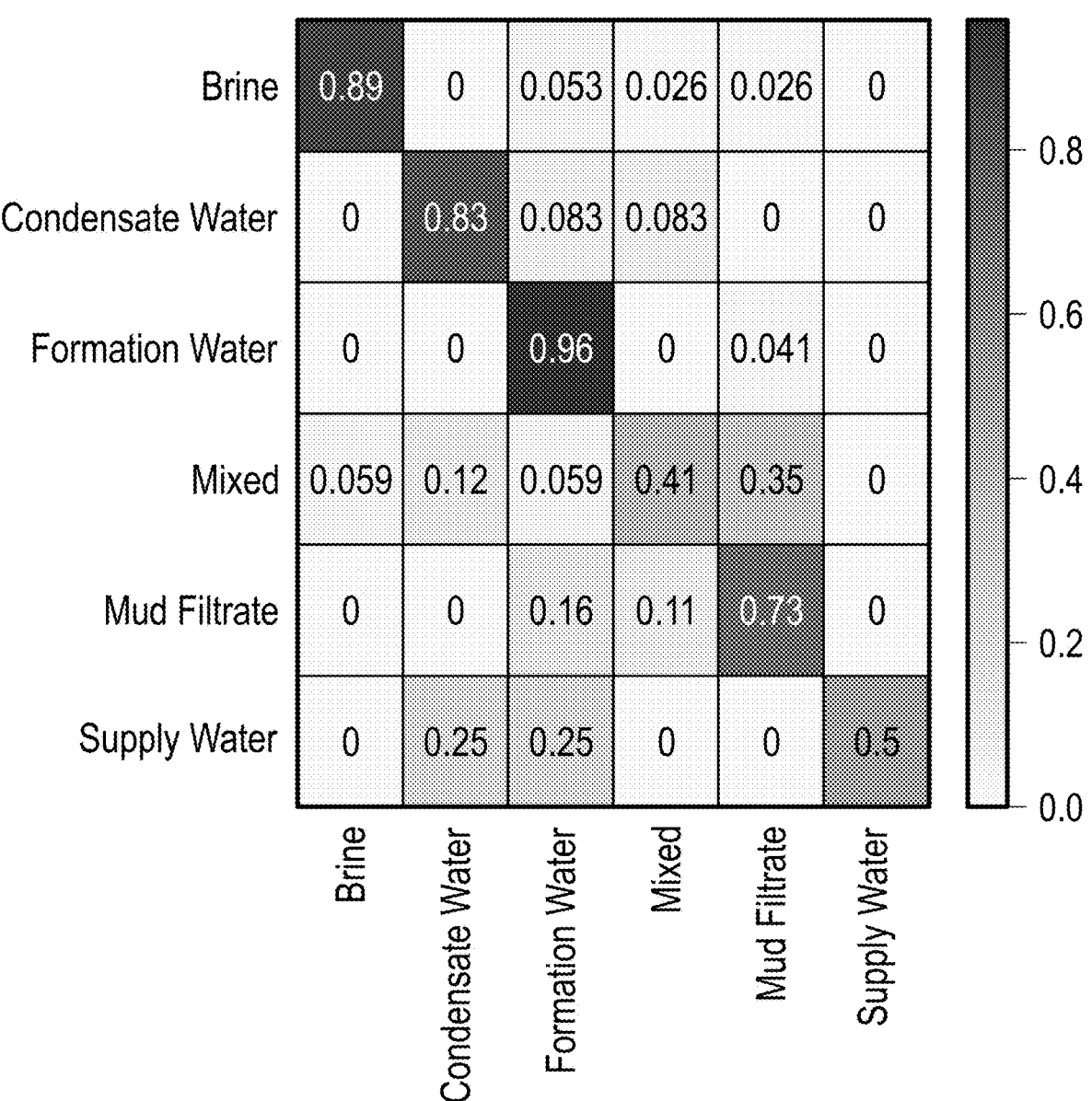
FIG. 5C depicts a feature importance plot, in accordance with one or more embodiments.
Figure 5D:
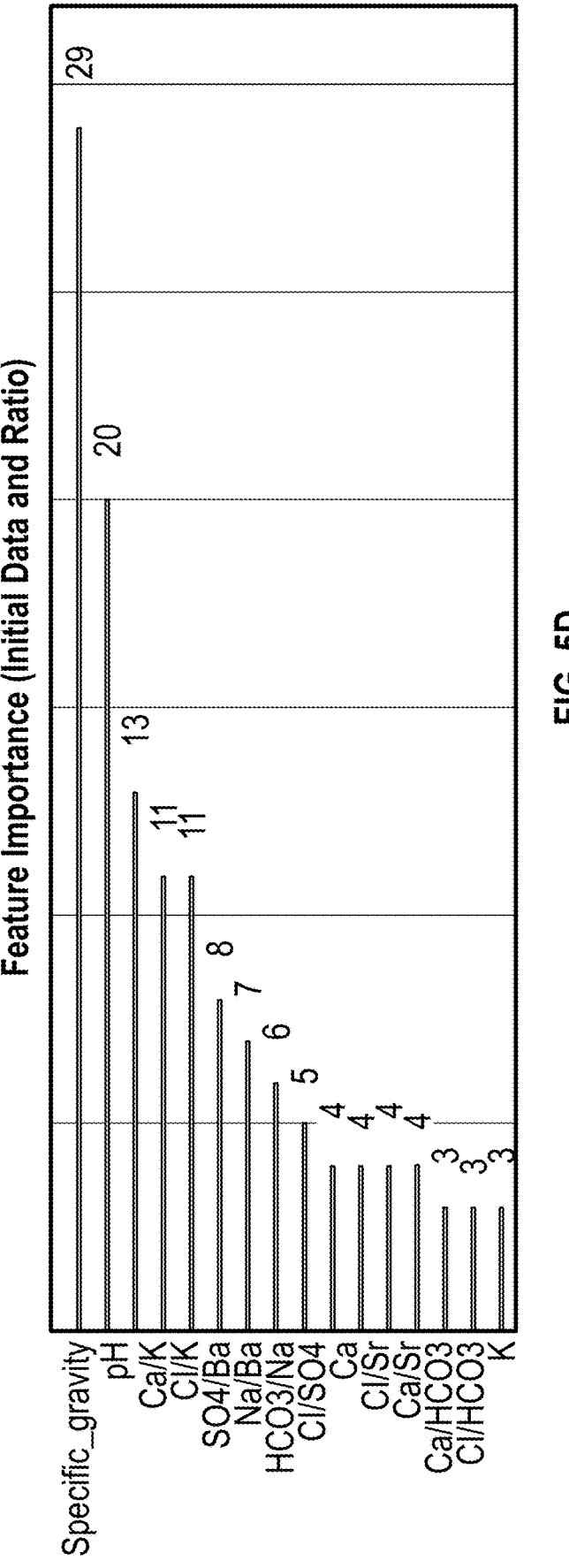
FIG. 5D depicts performance metrics for various types of machine-learned models, in accordance with one or more embodiments.

Continuing with the example, FIGS. 5B-5D depict, in greater detail, the results of the XGBoost machine-learned model. Specifically, FIG. 5B shows the prediction results for the first 5 produced water samples in the test set using the XGBoost model. As seen, the XGBoost model is configured to output the probability that a given water sample is of a water type, where the possible water types are: brine, condensate water, formation water, mixed, mud filtrate, and supply water. The predicted water type is determined by simply taking the water type with the highest predicted probability. For example, the probability that the first produced water sample in the test set is of the water type brine is 77.13%, as determined by the XGBoost machine-learned model. As such, the predicted water type, or the "predicted label", is brine. As seen in FIG. 5B, the predicted water types of the first 5 produced water samples in the test set are congruent with the expert-determined water types, or "true labels." FIG. 5C depicts a confusion matrix for the results of the XGBoost machine-learned model on the training set. The confusion matrix illustrates the proportion of correctly classified and misclassified samples. As seen, the greatest relative source of error currently comes from produced water samples of water type supply water being misidentified as either condensate water or formation water. An advantage of the XGBoost machine-learned model is that the so-called "feature importance" is easily determined and readily available for each input feature. A feature importance indicates the relative discriminatory power of a feature (i.e., how important a feature is in determining the prediction). FIG. 5D depicts the top 16 important features using the XGBoost machine-learned model. Interestingly, FIG. 5D demonstrates that of the most important features, the majority of them are derived features; indicative of the benefit of using the enhanced geochemical data.

In another concrete example, various semi-supervised algorithms were tested using an extended dataset containing geochemical data and expert classification for 777 produced water samples. The dataset was split into a training set containing 700 produced water samples and a test set containing 77 produced water samples. The semi-supervised algorithms require the selection of base algorithms for the self-training, co-training, and cluster-then-label approaches. For the self-training method, the XGBoost machine-learned model was chosen as the base algorithm. For the co-training method, XGBoost and random forest algorithms were used. For the cluster-then-label approach, agglomerative clustering was used as the clustering algorithm and XGBoost was applied as the classification algorithm. Further, a semi-supervised support vector machine (SVM) was also tested.

In instances of missing values in the dataset, the values were filled using a "mean" imputation strategy. The methods were trained using 4-fold cross-validation. The performance metrics of accuracy, precision, recall, and F1-score were calculated across the cross-validation folds. These metrics are tabulated in FIG. 6A. Based on the achieved results, the semi-supervised self-training method with accuracy 0.86, precision 0.87, recall 0.86, and F1-score 0.86 achieved the highest performance among all semi-supervised methods. The semi-supervised self-training method was then applied to the test set and the following metrics were achieved: accuracy 0.92, recall 0.92, precision 0.94, F1-score 0.93. Performance rate (the same as an accuracy) was equal to 92%.

Figures 6A, 6B:
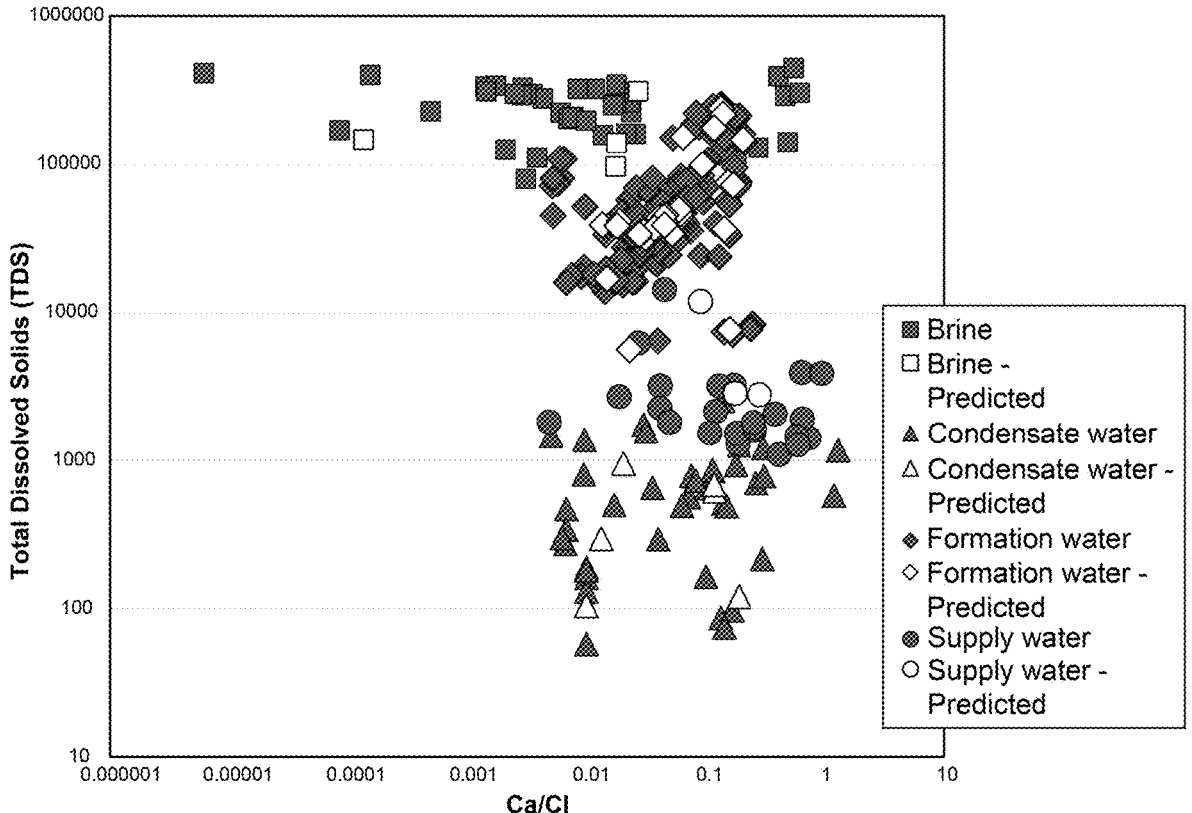
FIG. 6A depicts performance metrics, in accordance with one or more embodiments.
FIGS. 6B-6F depict a visualization of produced water samples and their assignment to water types with respect to various elemental ratios, in accordance with one or more embodiments.
Figures 6C, 6D:
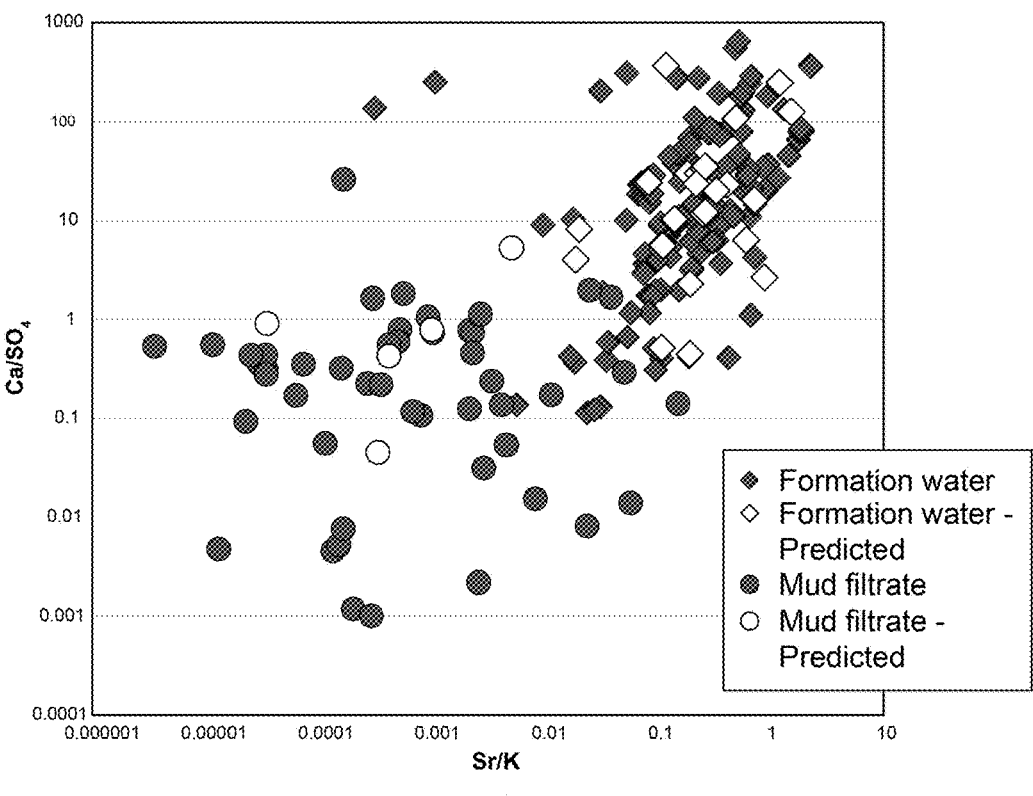
Figures 6E, 6F:
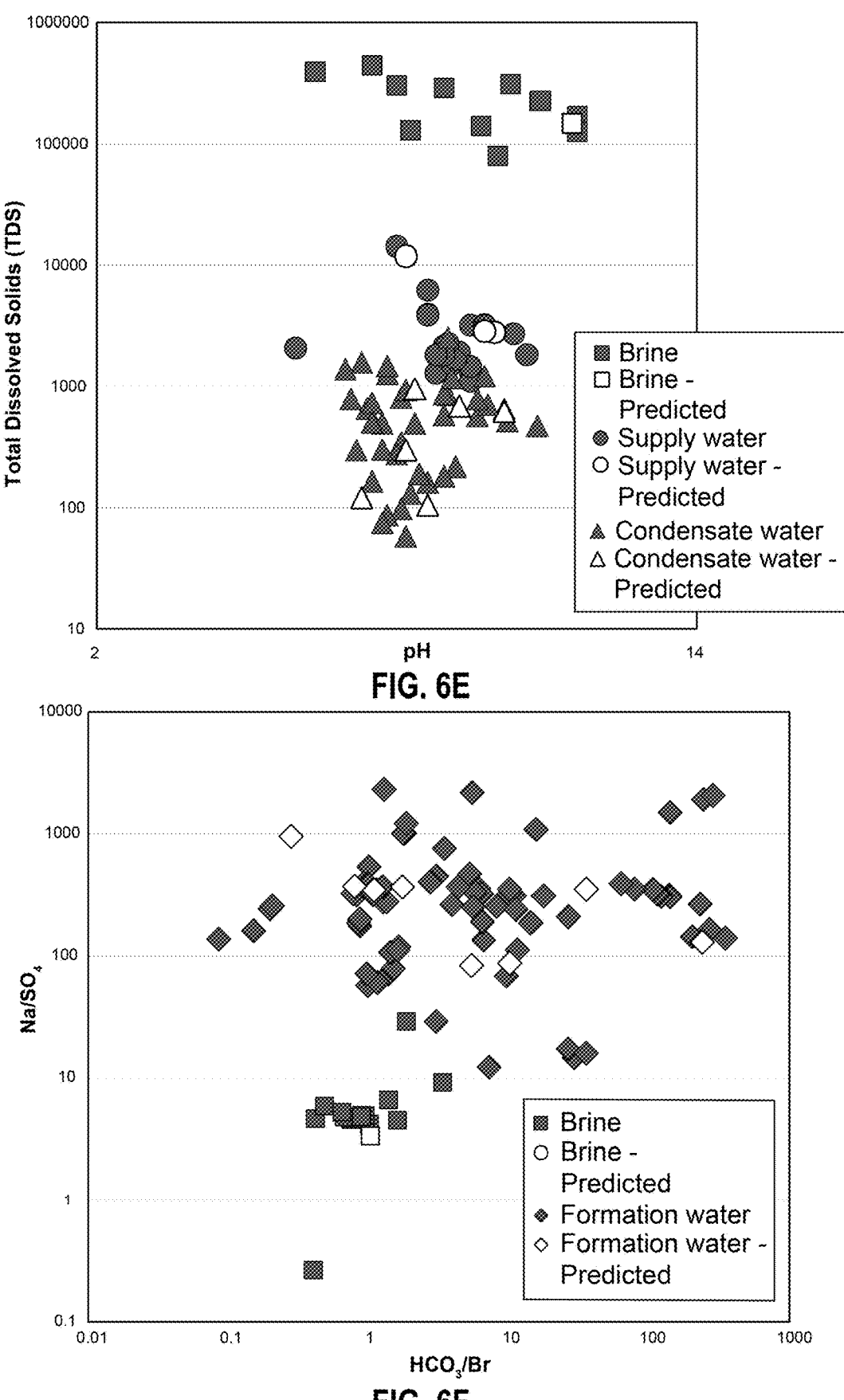

Continuing with the example, the elemental ratios of produced water samples were shown to be the most effective for a clustered separation of water types. FIGS. 6B to 6F show a visualization of elemental ratios from produced water samples and their assignment to separate sample clouds and water types for the above-mentioned training data set of 700 samples and testing data set of 77 samples. In FIGS. 6B to 6F the symbol shape indicates the water type—as determined by an expert for the training data and as predicted by the machine-learned model for the testing data. Further, the set (training or test) to which a data sample belongs is distinguished by "filling in" the symbols for the training data set and leaving the symbols for the testing data set unfilled. As shown in FIG. 6B, isolated water type clouds for formation water, completion brine, condensate water and supply water are formed by plotting Ca/Cl vs. total dissolved salinity (TDS), but some samples are still overlain in two groups. An optimum performance rate (>90%) for the grouping of all water types requires therefore the application of several ratios. As an example, Sr/K vs. Ca/SO$_4$ resulted to be a successful combination to distinguish formation water from mud filtrate (FIG. 6C), Ca/HCO$_3$ vs. Ca/Cl for the discrimination of formation water and condensate water (FIG. 6D), pH vs. TDS to separate completion brine, condensate water and supply water (FIG. 6E), and HCO$_3$/Br vs. Na/SO$_4$ to fingerprint completion brine and formation water (FIG. 6F). Drawing further attention FIG. 6D, all machine-learning classified samples of condensate water (unfilled triangles) fall within the compositional range of the expert-classified samples of condensate water (filled triangles), while all testing samples of formation water (unfilled rhombus) are aligned with formation water samples from the training dataset (filled rhombus), demonstrating the power of the elemental ratios Ca/HCO$_3$ and Ca/Cl to discriminate against condensate water and formation water.

The semi-supervised algorithm with the best performance rate was the XGBoost algorithm. Applied to the testing set this algorithm successfully classified the water types for 70 samples (out of 77) when compared to the classifications of an expert; an elevated performance rate of 89.7%. Further, the combination of unsupervised and semi-supervised techniques resulted to be a valid classification method for produced water with a satisfactory performance rate of about 90%.

Figure 7:
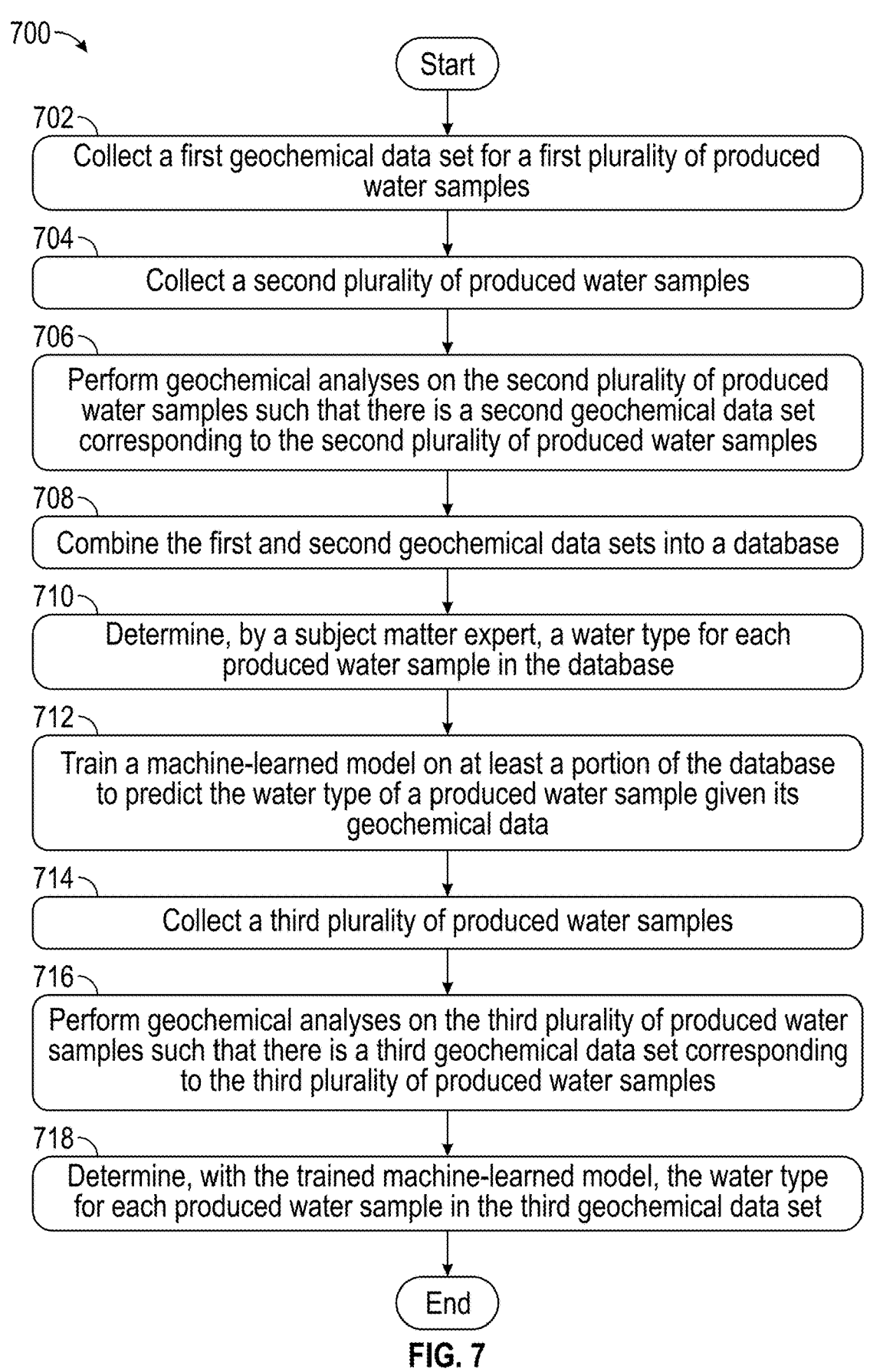
FIG. 7 depicts a flowchart, in accordance with one or more embodiments.

FIG. 7, in accordance with one or more embodiments, depicts the process of training and using a machine-learned model to determine the origin of produced water samples. In Block 702, a first geochemical data set for a first plurality of produced water samples is collected. In other words, for the first plurality of produced water samples, geochemical data already exists (e.g., a historical database). In Block 704, a second plurality of produced water samples is collected. As depicted in Block 706, geochemical analyses are performed on the second plurality of produced water samples such that there is a second geochemical data set corresponding to the second plurality of produced water samples. The first and second geochemical data sets are combined into a database, as shown in Block 708. In Block 710, a subject matter expert determines a water type for each produced water sample in the database. That is, the subject matter expert determines a water type for each produced water sample in both the first and second pluralities of produced water samples using, at least in part, their associated geochemical data sets. In Block 712, a machine-learned model is trained on at least a portion of the database (e.g., a training set) to predict the water type of a produced water sample given its geochemical data. It is noted that the geochemical data may undergo pre-processing or be augmented with derived features. In Block 714, a third plurality of produced water samples is collected. In Block 716, geochemical analyses are performed on the third plurality of produced water samples such that there is a third geochemical data set corresponding to the third plurality of produced water samples. The third geochemical data set may similarly undergo pre-processing and/or be augmented with derived features. In Block 718, the trained machine-learned model is used to determine the water type for each produced water sample in the third plurality of produced water samples using the third geochemical data set.

While the various blocks in FIGS. 3 and 7 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

Embodiments of the present disclosure may provide at least one of the following advantages. As previously discussed, the geochemical composition of produced water is linked to its origin. As such, analysis of samples of produced water may reveal key information about the underground system. For example, analysis of produced water throughout the life of the well may be used to determine, or at least estimate, fluid migration and reservoir compartmentalization. Further, identification of the origin of produced water may inform subsurface models such as regional salinity maps. Embodiments of the present disclosure teach using one or more machine-learned models to process geochemical data associated with a sample of produced water to determine the water type (indicative of the origin) of the sample. The disclosed embodiments describe methods for accurately determining if a produced water sample is of one of the following water types: formation water, supply water, brine, mixed, mud filtrate, condensate water. As such, embodiments disclosed herein overcome deficiencies of prior work in that they can identify many types of produced water as opposed to simply differentiating between artificial and natural fluids. Further, the disclosed embodiments demonstrate improved accuracy and are cost-effective.

Figure 8:
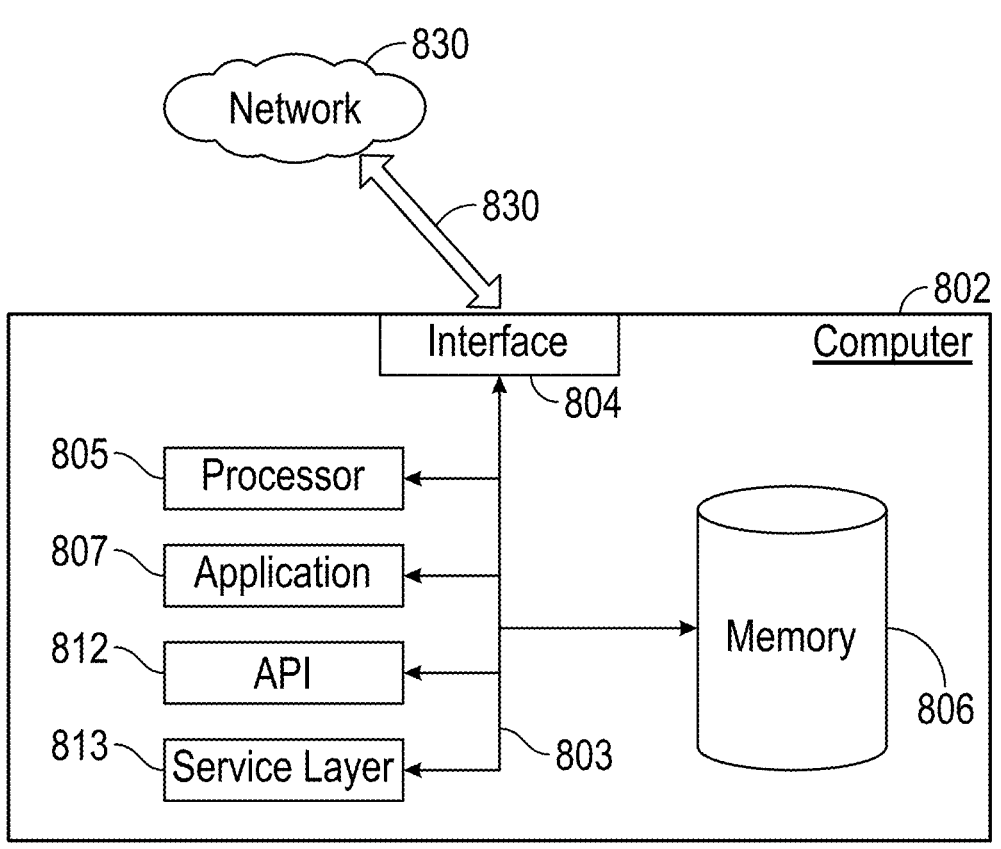
FIG. 8 depicts a system, in accordance with one or more embodiments.

FIG. 8 further depicts a block diagram of a computer system (802) used to provide computational functionalities associated with the algorithms, methods, functions, processes, flows, and procedures as described in this disclosure, according to one or more embodiments. The illustrated computer (802) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (802) may include a computer that includes an input device, such as a keypad, keyboard, touch screen, or other device that can accept user information, and an output device that conveys information associated with the operation of the computer (802), including digital data, visual, or audio information (or a combination of information), or a GUI.

The computer (802) can serve in a role as a client, network component, a server, a database or other persistency, or any other component (or a combination of roles) of a computer system for performing the subject matter described in the instant disclosure. In some implementations, one or more components of the computer (802) may be configured to operate within environments, including cloud-computing-based, local, global, or other environment (or a combination of environments).

At a high level, the computer (802) is an electronic computing device operable to receive, transmit, process, store, or manage data and information associated with the described subject matter. According to some implementations, the computer (802) may also include or be communicably coupled with an application server, e-mail server, web server, caching server, streaming data server, business intelligence (BI) server, or other server (or a combination of servers).

The computer (802) can receive requests over network (830) from a client application (for example, executing on another computer (802) and responding to the received requests by processing the said requests in an appropriate software application. In addition, requests may also be sent to the computer (802) from internal users (for example, from a command console or by other appropriate access method), external or third-parties, other automated applications, as well as any other appropriate entities, individuals, systems, or computers.

Each of the components of the computer (802) can communicate using a system bus (803). In some implementations, any or all of the components of the computer (802), both hardware or software (or a combination of hardware and software), may interface with each other or the interface (804) (or a combination of both) over the system bus (803) using an application programming interface (API) (812) or a service layer (813) (or a combination of the API (812) and service layer (813). The API (812) may include specifications for routines, data structures, and object classes. The API (812) may be either computer-language independent or dependent and refer to a complete interface, a single function, or even a set of APIs. The service layer (813) provides software services to the computer (802) or other components (whether or not illustrated) that are communicably coupled to the computer (802). The functionality of the computer (802) may be accessible for all service consumers using this service layer. Software services, such as those provided by the service layer (813), provide reusable, defined business functionalities through a defined interface. For example, the interface may be software written in JAVA, C++, or other suitable language providing data in extensible markup language (XML) format or another suitable format. While illustrated as an integrated component of the computer (802), alternative implementations may illustrate the API (812) or the service layer (813) as stand-alone components in relation to other components of the computer (802) or other components (whether or not illustrated) that are communicably coupled to the computer (802). Moreover, any or all parts of the API (812) or the service layer (813) may be implemented as child or sub-modules of another software module, enterprise application, or hardware module without departing from the scope of this disclosure.

The computer (802) includes an interface (804). Although illustrated as a single interface (804) in FIG. 8, two or more interfaces (804) may be used according to particular needs, desires, or particular implementations of the computer (802). The interface (804) is used by the computer (802) for communicating with other systems in a distributed environment that are connected to the network (830). Generally, the interface (804) includes logic encoded in software or hardware (or a combination of software and hardware) and operable to communicate with the network (830). More specifically, the interface (804) may include software supporting one or more communication protocols associated with communications such that the network (830) or interface's hardware is operable to communicate physical signals within and outside of the illustrated computer (802).

The computer (802) includes at least one computer processor (805). Although illustrated as a single computer processor (805) in FIG. 8, two or more processors may be used according to particular needs, desires, or particular implementations of the computer (802). Generally, the computer processor (805) executes instructions and manipulates data to perform the operations of the computer (802) and any algorithms, methods, functions, processes, flows, and procedures as described in the instant disclosure.

The computer (802) also includes a memory (806) that holds data for the computer (802) or other components (or a combination of both) that can be connected to the network (830). The memory may be a non-transitory computer readable medium. For example, memory (806) can be a database storing data consistent with this disclosure. Although illustrated as a single memory (806) in FIG. 8, two or more memories may be used according to particular needs, desires, or particular implementations of the computer (802) and the described functionality. While memory (806) is illustrated as an integral component of the computer (802), in alternative implementations, memory (806) can be external to the computer (802).

The application (807) is an algorithmic software engine providing functionality according to particular needs, desires, or particular implementations of the computer (802), particularly with respect to functionality described in this disclosure. For example, application (807) can serve as one or more components, modules, applications, etc. Further, although illustrated as a single application (807), the application (807) may be implemented as multiple applications (807) on the computer (802). In addition, although illustrated as integral to the computer (802), in alternative implementations, the application (807) can be external to the computer (802).

There may be any number of computers (802) associated with, or external to, a computer system containing computer (802), wherein each computer (802) communicates over network (830). Further, the term "client," "user," and other appropriate terminology may be used interchangeably as appropriate without departing from the scope of this disclosure. Moreover, this disclosure contemplates that many users may use one computer (802), or that one user may use multiple computers (802).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plusfunction clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112 (f) for any limitations of any of the claims herein, except for those in which the claim expressly uses the words 'means for' together with an associated function.

What is claimed is:

1. A method, comprising:
collecting a first geochemical data set comprising geochemical data for a first plurality of produced water samples;
collecting a second plurality of produced water samples from an oil and gas field;
performing a geochemical analysis on the second plurality of produced water samples to form a second geochemical data set, wherein the second geochemical data set comprises geochemical data for the second plurality of produced water samples;
combining the first geochemical data set and the second geochemical data set into a database;
determining, by a subject matter expert, a water type for each produced water sample in the database;
training a machine-learned model on at least a portion of the database to predict the water type of a produced water sample given its geochemical data;
collecting a third plurality of produced water samples from a well of the oil and gas field that penetrates a subsurface of the oil and gas field;
performing the geochemical analysis on the third plurality of produced water samples to form a third geochemical data set, wherein the third geochemical data set comprises geochemical data for the third plurality of produced water samples;
determining, with the trained machine-learned model, the water type for each produced water sample in the third plurality of produced water samples using the third geochemical data set;
generating a regional salinity map for the subsurface based on the determined water type for each produced water sample in the third plurality of produced water samples; and
adjust a production operation of the well based on the regional salinity map.

2. The method of claim 1, further comprising:
augmenting geochemical data with derived data; and
pre-processing the geochemical data.

3. The method of claim 1, wherein the machine-learned model is a supervised gradient boosting classifier.

4. The method of claim 1, wherein the machine-learned model is a semi-supervised gradient boosting classifier.

5. The method of claim 1, further comprising:
selecting a machine-learned model type and hyperparameters;
evaluating the trained machine-learned model;
adjusting the machine-learned model hyperparameters; and
re-training the trained machine learned model with the adjusted machine-learned model hyperparameters.

6. The method of claim 1, further comprising estimating the generalization error of the machine-learned model.

7. The method of claim 1, wherein the water types comprise: brine, formation water, mixed, mud filtrate, condensate water, and supply water.

8. The method of claim 1, the well having been previously drilled using a drilling system, wherein drilling the well comprised injecting a drilling fluid into the subsurface.

9. A non-transitory computer readable medium storing instructions executable by a computer processor, the instruction comprising functionality for:
receiving a first geochemical data set comprising geochemical data for a first plurality of produced water samples;
receiving a second geochemical data set for a second plurality of produced water samples from an oil and gas field, wherein the second geochemical data set comprises geochemical data for the second plurality of produced water samples;
combining the first geochemical data set and the second geochemical data set into a database;
receiving a water type for each produced water sample in the database, wherein the water type is determined by a subject matter expert;
training a machine-learned model on at least a portion of the database to predict the water type of a produced water sample given its geochemical data;
receiving a third geochemical data set for a third plurality of produced water samples from a well of the oil and gas field that penetrates a subsurface of the oil and gas field wherein the third geochemical data set comprises geochemical data for the third plurality of produced water samples;
determining, with the trained machine-learned model, the water type for each produced water sample in the third plurality of produced water samples using the third geochemical data set;
generating a regional salinity map for the subsurface based on the determined water type for each produced water sample in the third plurality of produced water samples; and
commanding an adjustment to a production operation of the well based on the regional salinity map.

10. The non-transitory computer readable medium of claim 9, the instructions further comprising functionality for:
augmenting geochemical data with derived data; and
pre-processing the geochemical data.

11. The non-transitory computer readable medium of claim 9, wherein the machine-learned model is a supervised gradient boosting classifier.

12. The non-transitory computer readable medium of claim 9, wherein the machine-learned model is a semi-supervised gradient boosting classifier.

13. The non-transitory computer readable medium of claim 9, the instructions further comprising functionality for:
selecting a machine-learned model type and architecture;
evaluating the trained machine-learned model;
adjusting the machine-learned model architecture; and
re-training the trained machine learned model with the adjusted machine-learned model architecture.

14. The non-transitory computer readable medium of claim 9, wherein the machine-learned model determines that the water type is one of: brine, formation water, mixed, mud filtrate, condensate water, and supply water.

15. A system, comprising:
a first geochemical data set comprising geochemical data for a first plurality of produced water samples;

a second plurality of produced water samples from an oil and gas field;

a second geochemical data set, wherein the second geochemical data set comprises geochemical data for the second plurality of produced water samples;

a third plurality of produced water samples having been acquired from a well of the oil and gas field that penetrates a subsurface of the oil and gas field;

a third geochemical data set, wherein the third geochemical data set comprises geochemical data for the third plurality of produced water samples;

a plurality of water types, wherein the plurality of water types comprises a water type for each produced water sample in both the first and second pluralities of produced water samples, and wherein the water type for each produced water sample was determined by a subject matter expert;

a trained machine-learned model; and a computer, the computer comprising:

one or more computer processors, and a non-transitory computer readable medium storing instructions executable by a computer processor, the instructions comprising functionality for:

processing, with the trained machine-learned model, the third geochemical data set to determine a water type for each produced water sample in the third plurality of produced water samples, generating a regional salinity map for the subsurface based on the determined water type for each produced water sample in the third plurality of produced water samples, and commanding an adjustment to a production operation of the well based on the regional salinity map.

16. The system of claim 15, wherein the instructions further comprising functionality for:

augmenting geochemical data with derived data; and pre-processing the geochemical data.

17. The system of claim 15, wherein the trained machine-learned model is a supervised gradient boosting classifier.

18. The system of claim 15, wherein the trained machine-learned model is a semi-supervised gradient boosting classifier.

19. The system of claim 15, wherein the trained machine-learned model determines that the water type is one of: brine, formation water, mixed, mud filtrate, condensate water, and supply water.

20. The system of claim 15, further comprising a drilling system, wherein the well having been previously drilled using the drilling system, wherein drilling the well comprised injecting a drilling fluid into the subsurface.

* * * * *